(12) United States Patent
Zell

(10) Patent No.: US 12,144,905 B1
(45) Date of Patent: Nov. 19, 2024

(54) KIOSK SCREEN DISINFECTING SYSTEM

(71) Applicant: Elizabeth T. Zell, Farmdale, OH (US)

(72) Inventor: Elizabeth T. Zell, Farmdale, OH (US)

( * ) Notice: Subject to any disclaimer, the term of this patent is extended or adjusted under 35 U.S.C. 154(b) by 561 days.

(21) Appl. No.: 17/565,072

(22) Filed: Dec. 29, 2021

Related U.S. Application Data

(60) Provisional application No. 63/131,775, filed on Dec. 29, 2020.

(51) Int. Cl.
*A61L 2/18* (2006.01)
*A61L 101/34* (2006.01)
*G06Q 20/18* (2012.01)

(52) U.S. Cl.
CPC ............. *A61L 2/18* (2013.01); *G06Q 20/18* (2013.01); *A61L 2101/34* (2020.08); *A61L 2202/15* (2013.01)

(58) Field of Classification Search
CPC .... A61L 2/18; A61L 2101/34; A61L 2202/15; G06Q 20/18
See application file for complete search history.

(56) References Cited

U.S. PATENT DOCUMENTS

| | | | | |
|---|---|---|---|---|
| 4,485,588 A | * | 12/1984 | Reed | A01M 21/043 47/1.7 |
| 5,550,564 A | | 8/1996 | Cragun | |
| 6,766,553 B2 | * | 7/2004 | Wilson | B60S 1/3882 15/250.04 |
| 6,944,904 B1 | * | 9/2005 | Williams | B43L 21/02 15/97.1 |
| 7,503,091 B2 | * | 3/2009 | White, Jr. | A47L 1/02 15/103 |
| 8,597,569 B2 | | 12/2013 | Gruen et al. | |
| 8,695,152 B2 | | 4/2014 | Lemchen | |
| 9,028,962 B2 | | 5/2015 | Borrelli et al. | |
| 9,392,853 B2 | | 7/2016 | Lawler | |
| 9,612,712 B2 | * | 4/2017 | Huebner | G06F 3/0481 |
| 10,304,147 B2 | | 5/2019 | Kelly et al. | |
| 2007/0026089 A1 | | 2/2007 | Hu | |
| 2015/0292126 A1 | | 10/2015 | Prosser | |
| 2021/0369885 A1 | * | 12/2021 | Lee | A61L 2/26 |

FOREIGN PATENT DOCUMENTS

| | | | |
|---|---|---|---|
| CN | 210924351 U | | 7/2020 |
| CN | 211349238 U | | 8/2020 |
| CN | 211555059 U | * | 9/2020 |

\* cited by examiner

*Primary Examiner* — Jennifer Wecker
*Assistant Examiner* — Brady C Pilsbury
(74) *Attorney, Agent, or Firm* — Invention To Patent Services; Alex Hobson

(57) ABSTRACT

A kiosk disinfecting system for large walk-up kiosk screens utilizing touchscreens applies a disinfecting fluid to the touchscreen and has a means to move a wiper over the screen to disinfect the touchscreen. A controller may detect the presence of a user and may automatically activate a disinfecting cycle to ensure that the touchscreen is disinfected between users. The disinfecting system may have a disinfecting fluid applicator, such a spray nozzle(s) and a wiper assembly that makes contact with the touchscreen to spread the disinfecting fluid over the touchscreen surface. A wiper may be a wick-wiper that absorbs or wick disinfecting fluid from a reservoir through the wick to the touchscreen. A very small area of the wick may extend out from an applicator opening to reduce the amount of disinfecting fluid that evaporates over time. A disinfection fluid may be non-volatile and may be all natural and food safe.

17 Claims, 11 Drawing Sheets

KIOSK SCREEN DISINFECTING SYSTEM

CROSS REFERENCE TO RELATED APPLICATION

This application claims the benefit of priority to U.S. provisional patent application No. 63/131,775, filed on Dec. 29, 2020; the entirety of which is hereby incorporated by reference herein.

BACKGROUND OF THE INVENTION

Field of the Invention

The invention relates to a kiosk disinfecting system for large walk-up kiosk screens, touch screens, having a height of at least 40 cm and a width of at least 30 cm.

Background

Kiosks touch screens are often used in establishments for customers to place an order, or enter information prior to an appointment. For example, restaurants, such fast-food restaurants, are more routinely using kiosk touch screens for order entry and payment of orders. The kiosk may print out a ticket or receipt with an order number and the customer will retrieve their order using the ticket. These kiosks usually utilize touchscreens as a user interface which can be places where pathogens are passed from one customer to another. The establishment or business may have personnel clean or disinfect the screens periodically but this is expensive, unreliable and impractical between each customer.

Some disinfectants include volatile fluids that have a strong smell. In addition, many disinfectants are flammable. Manual disinfecting or cleaning with volatile disinfectants may lead to an offensive smell and/or a hazardous condition. An establishment with many kiosks may be reluctant to clean the touchscreens regularly because of these drawbacks. A customer may be displeased with eating their food in an establishment that smells like disinfectant. Also, some people have allergic reactions to volatile compounds. It would not be desirable to produce these undesirable conditions in a business establishment as it would drive away customers.

SUMMARY OF THE INVENTION

The invention is directed to a kiosk disinfecting system for large walk-up kiosk touch screens having a height of at least 40 cm and a width of at least 30 cm. An exemplary kiosk disinfecting system utilizes a disinfecting fluid that is applied to the touchscreen and dispersed over the touchscreen surface to effectively disinfect the surface, whereby at least 90% of all pathogens are inactivated. An exemplary kiosk disinfecting system may comprise a fluid applicator and a wiper assembly that makes contact with the touchscreen to disperse or spread the disinfecting fluid over the touchscreen surface.

An exemplary kiosk disinfecting system may have a user sensor to detect the presence of a user proximal to the kiosk screen which may initiate a disinfecting cycle. A controller may be coupled with the user sensor and may initiate a disinfecting cycle upon the detection of a user approaching the kiosk, or when a user is detected for some time and then departs from the kiosks. A controller may also be coupled with the user interface and may detect when an order or entry has been made by a user on the kiosk. The controller may then wait for the user to depart from the kiosk, as determined by the user sensor before a disinfecting cycle is activated. A message may be displayed on the kiosk touch screen that a disinfecting cycle is in progress, or to please wait for the disinfecting cycle to finish before placing an order, for example.

An exemplary kiosk disinfecting system may have a payment interface that enables a user to make a payment for an order to complete the order. An exemplary payment interface may include a payment reader, such as a credit card reader, a phone reader for paying with a phone or other electronic device and the like. The controller may initiate a disinfecting cycle upon receipt of payment or upon the removal of the ticket or receipt from the kiosk. In this way, the touchscreen will be cleaned before the next user.

In an exemplary embodiment, the kiosk disinfecting system comprises a manual handle on the wiper assembly that may be used to manually clean the touchscreen by moving the wiper assembly up and down over the screen. In an exemplary embodiment, the ticket or receipt will not print or be provided until the screen is manually cleaned by the user moving the wiper assembly up and down over the screen. The touchscreen may instruct the user to move the handle down and/or up as required before the ticket is provided, for example.

An exemplary kiosk disinfecting system may utilize a fluid applicator, to dispense fluid onto the touchscreen before it is dispersed or spread. An exemplary fluid applicator may be a spray applicator, wherein the disinfecting fluid is sprayed onto the touchscreen. A fluid applicator may utilize a plurality of spray nozzles to provide adequate application of the disinfecting fluid onto the touchscreen. An exemplary kiosk disinfecting system may utilize a wiper to disperse or spread the sprayed-on disinfectant. A wiper may be coupled with a wiper reservoir and any excess disinfecting fluid may be retained in the wiper reservoir.

An exemplary wiper may be actuated to move across the touchscreen by a wiper actuator. An exemplary wiper actuator moves the wiper assembly and the wiper up and down along the touchscreen. The fluid applicator may apply the disinfecting fluid to the top of the touchscreen and the wiper may wipe the disinfecting fluid down over the touchscreen. This configuration utilizes gravity to help with spreading and dispersing the disinfecting fluid. The fluid applicator may be configured above or below the wiper.

An exemplary wiper may be supple or pliable and may be pressed and deflect against the touchscreen surface. This soft and pliable wiper may effectively spread the disinfecting fluid while preventing damage to the touchscreen. An exemplary wiper may be an elastomeric material, such as a rubber or silicone material. An exemplary wiper may be a foam, such as an open-celled foam that may wick in and then spread the fluid over the touchscreen surface, or a closed cell foam that conforms and deflects against the touchscreen surface but does not absorb the disinfecting fluid.

A fluid applicator may utilize a wick-wiper, that wicks disinfecting fluid into the wick-wiper that is configured to move across the touchscreen to effectively disperse or spread the disinfectant. A wick-wiper may wick disinfecting fluid from a wiper reservoir and an exposed portion of the wick wiper may be pressed against the touchscreen for dispersing the disinfecting fluid. A wiper reservoir may be filled from a disinfecting fluid reservoir and a sensor may detect when the wiper reservoir drops below a threshold level. Note that a kiosk may have a single disinfecting fluid reservoir that acts or is used as the wiper reservoir. In an exemplary embodiment, a wick-wiper has a vertical extension portion that extends up from the liquid disinfectant before extending through an applicator opening in the wiper reservoir to the expose wick wiper. In this embodiment, the wick-wiper wicks disinfectant up through the vertical extension portion through capillary force. This configuration may prevent any leaking of the disinfectant from the fluid applicator housing.

A wick-wiper may extend out from the wiper assembly through an applicator opening and this opening may be kept small to prevent disinfecting fluid from evaporating out of the reservoir. An applicator opening height may be no more than about 1 cm, or no more than about 2.0 cm or no more than about 2.5 cm. Again, the applicator opening may extend across the width of the touchscreen.

An exemplary wick-wiper may be material that wicks fluid through pores or cells within the material and may be a woven or non-woven material or a foam, for example. A woven material may have a particular weave to ensure effective wicking of disinfecting fluid and may have tighter pores or capillaries for wicking than a foam. A wick-wiper may use a first type of wicking material to draw the disinfecting fluid from a reservoir and may use a second type of wick material as a contact with the touchscreen. A portion of the wick-wiper may have cover such as the exposed wick wiper, and this cover may provide a contact surface with the touchscreen.

An exemplary disinfecting fluid may be a volatile compound that includes alcohol or other volatile hydrocarbon that effectively disinfects surfaces, such as isopropyl alcohol or ethanol. Disinfectants that may be used include any included in the Environmental Protection Agency, List N: Disinfectants for Use Against SARS-CoV-2 (COVID-19), as published or accessed on Dec. 18, 2020. Some specific disinfectants from this list that may be effective in kiosk disinfecting application include, but are not limited to, EPA Registration No. 92987-1, sodium chlorite and citric acid, Registration No. 50755-5, citric acid, and EPA Registration No 90276-1, sodium hypochlorite. An exemplary volatile disinfectant comprises alcohol, such as ethyl alcohol or isopropyl alcohol, which may be included in a volumetric concentration of about 50% or more, 70% or more, 80% or more, and even 90% or more. As described herein, volatile disinfecting fluids may cause undesirable odors and reactions, especially when an establishment has a plurality of kiosks. Therefore, it may be desirable to minimize the amount of the volatile disinfecting fluid that volatilizes. This may be accomplished by using a wick-wiper, wherein only a small area of the wick-wiper, the exposed wick wiper, is exposed and therefore is prone to volatilization of the disinfecting fluid. Also, the wick reservoir and the disinfecting fluid reservoir may be sealed to prevent the disinfectant from volatilizing. A preferred disinfectant is not volatile or has low volatility and is safe human contact. However, when a wick-wiper is used allow exposed surface area of the wick is produced and therefore a volatile disinfecting fluid may be suitable and preferred.

Another type of disinfecting fluid may be a low pH disinfectant that utilizes an acidic compound with water, such as vinegar. An exemplary low pH disinfectant may have a pH of no more than about 4.5, or no more than 4.0, or no more than 3.5 and the like. An exemplary disinfecting fluid may be an all-natural disinfecting fluid and may contain, hypochlorous acid and/or sodium hydroxide.

An exemplary kiosk touchscreen may be a large walk-up touchscreen having a height of about 40 cm or more, about 60 cm or more, about 80 cm or more and any range between and including the height values provided. The kiosk touchscreen may have a width of about 30 cm or more, about 40 cm or more, about 60 cm or more, or even about 80 cm or more and any range between and including the width values provided.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
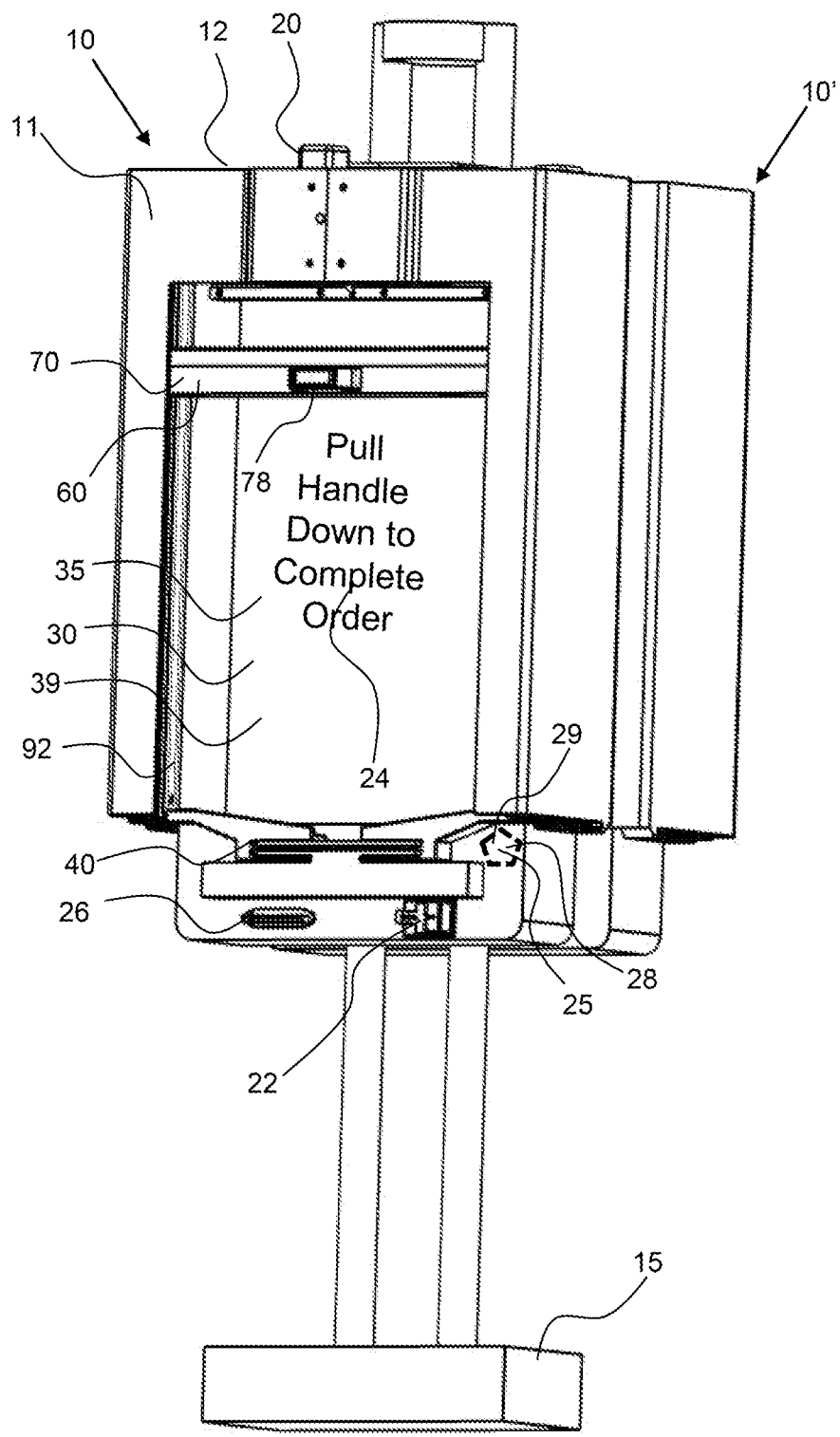
FIG. 1 shows a perspective view of an exemplary kiosk screen disinfecting system having a fluid applicator to dispense a disinfecting fluid onto a kiosk screen and a wiper assembly that moves a wiper over the kiosk screen to spread the disinfecting fluid over the kiosk screen.
Figure 2:
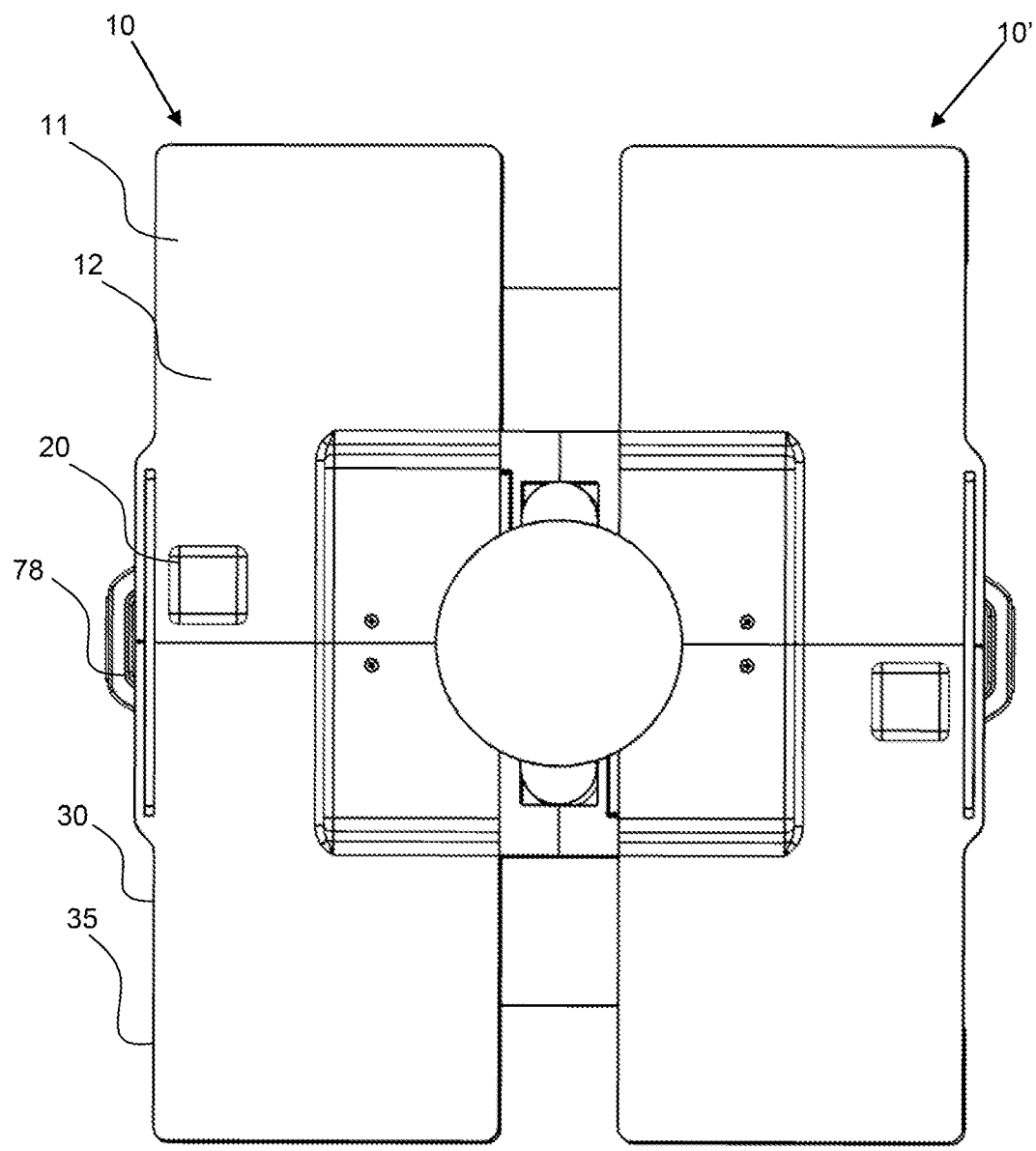
FIG. 2 shows a top view of an exemplary kiosk screen disinfecting system having a user sensor to detect a user and to activate a disinfecting cycle of the kiosk screen.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Referring now to FIGS. 1 to 4, an exemplary kiosk screen disinfecting system 10 is configured in a housing 11 for retaining the kiosk screen 30, which is a display screen 39 and a touch screen 35. A display screen is an electronic display screen, such as a monitor. A fluid applicator 60 is configured to dispense a disinfecting fluid onto a kiosk screen and a wiper assembly 70 is configured to move a wiper such as a wick-wiper, over the kiosk screen to spread the disinfecting fluid over the kiosk screen. A user sensor 20 is configured on the top 12 of the housing and is configured to detect when a user is proximal to the kiosk screen. The sensor may be a motion sensor. The fluid applicator and the wiper assembly may be activated by the detection of a user or when the user moves away from the kiosk. The kiosk screen disinfecting system has a payment interface 22 to allow the user to make a payment for products selected on the kiosk. An exemplary kiosk screen disinfecting system may also have a receipt dispenser 26 to dispense a receipt that can be used to pick-up products purchased.

As shown in FIGS. 1 to 4, two exemplary kiosk screen disinfecting systems 10, 10' are coupled together and supported by a common stand 15. Each of the kiosk screen disinfecting systems may have a controller 25, that may include a microprocessor 28 or computer 29 that controls the functions of the system. The controller may receive input from the user sensor and may activate disinfecting of the kiosk screen and may interface with an order fulfillment system, such as to for food orders at a restaurant, for example. Also, the controller may process transactions for payment for products ordered. The controller may produce a display message 24 on the display screen 39 instructing the user to disinfect the screen via the manual handle 78 before the order will be placed and completed, as shown in FIG. 1.

Figure 3:
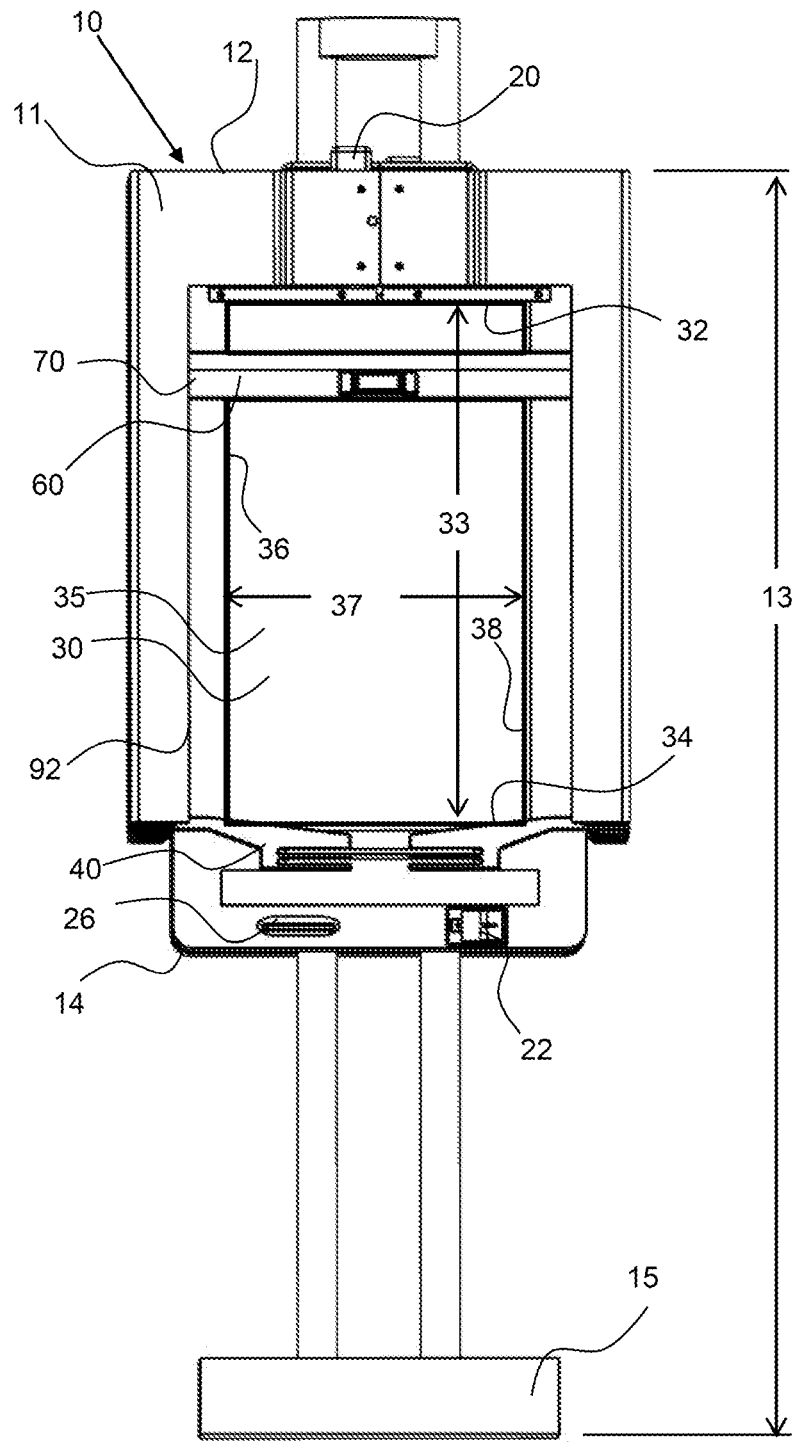
FIG. 3 shows a front view of an exemplary kiosk screen disinfecting system having a fluid applicator to dispense a disinfecting fluid onto a kiosk screen and a wiper assembly that moves a wiper over the kiosk screen to spread the disinfecting fluid over the kiosk screen.
Figure 4:
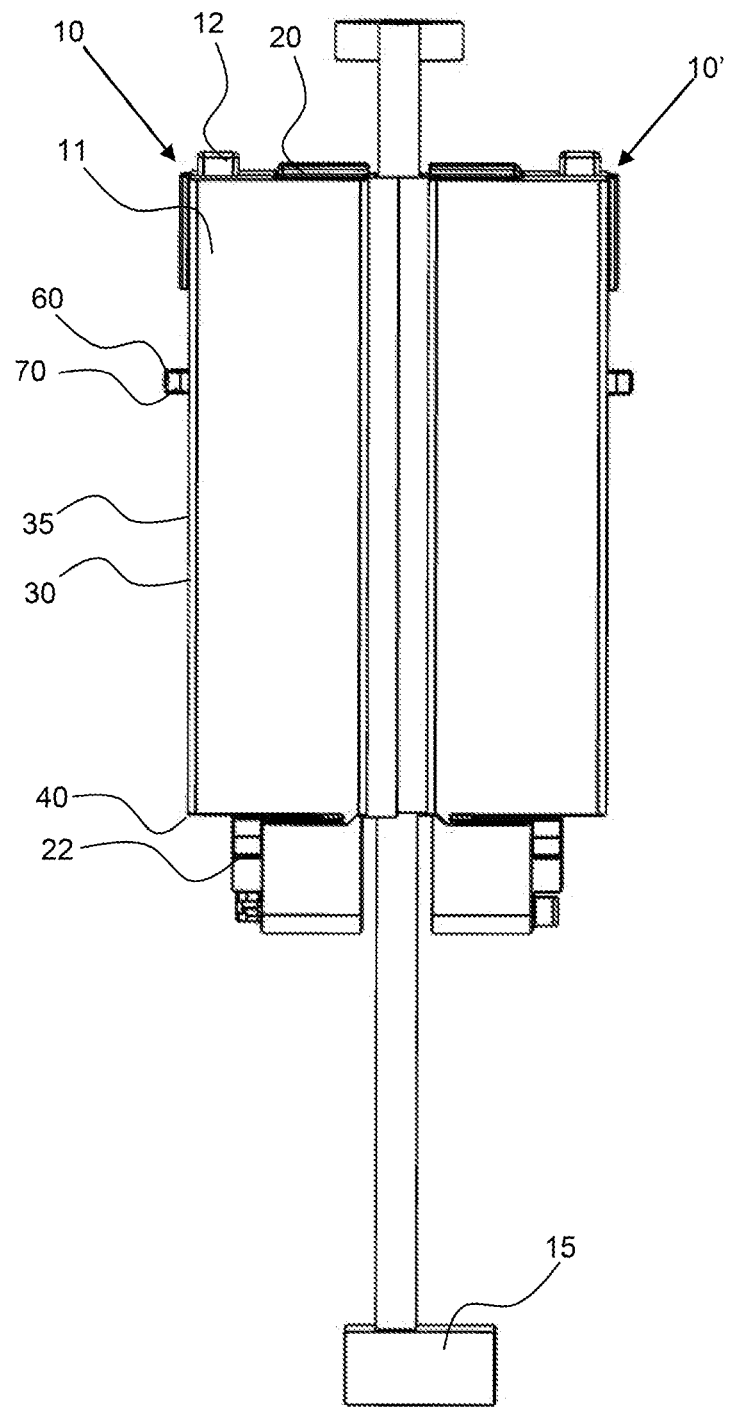
FIG. 4 shows a side view of two exemplary kiosk screen disinfecting systems coupled together for use by two users on opposing sides.

A collection reservoir 40 is configured proximal to the bottom of the kiosk screen to collect any disinfecting fluid that may be wiped down by the wiper. The kiosk screen has a height 33 from a bottom 34 to a top 32, and a width 37 from a left side 36 to a right side 38, as shown in FIG. 3 and as described herein. The height 13 of the kiosk screen disinfecting system from the base to the top of the housing 11 may be about 1 m or more, about 1.25 m or more, about 1.5 m or more, about 2 m or more and any range between and including the heights provided. The kiosk screen disinfecting system may be self-standing and configured on a stand 15, as shown.

The fluid applicator 60 and wiper assembly 70 may be configured to be moved up and down manually, by the manual handle 78, or may be configured to move automatically by a wiper actuator 90 that may comprise a motor and one or more gears and described herein.

Figure 5:
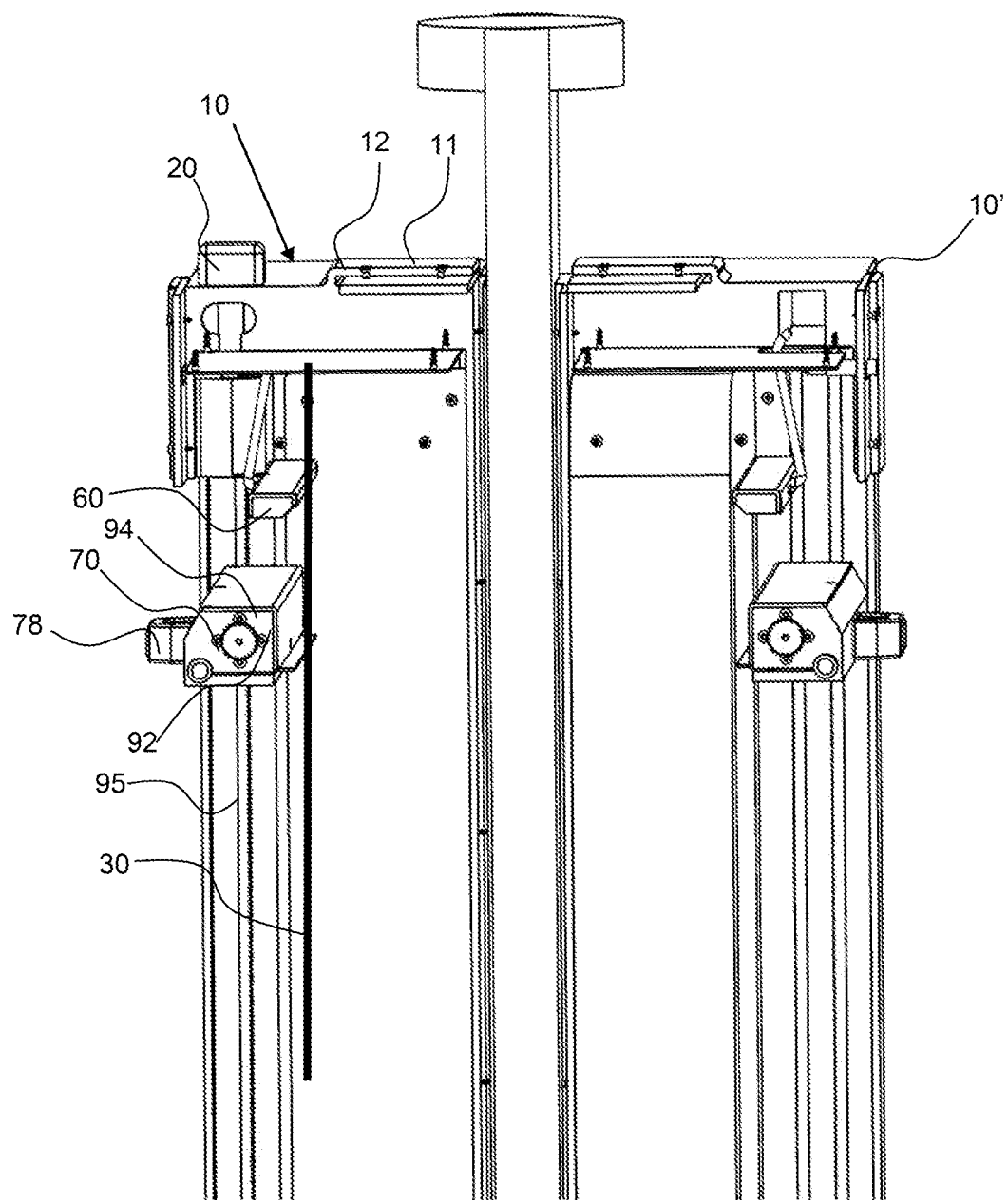
FIG. 5 shows a cross sectional view of the fluid applicator and wiper assembly of an exemplary kiosk screen disinfecting system.
Figure 6:
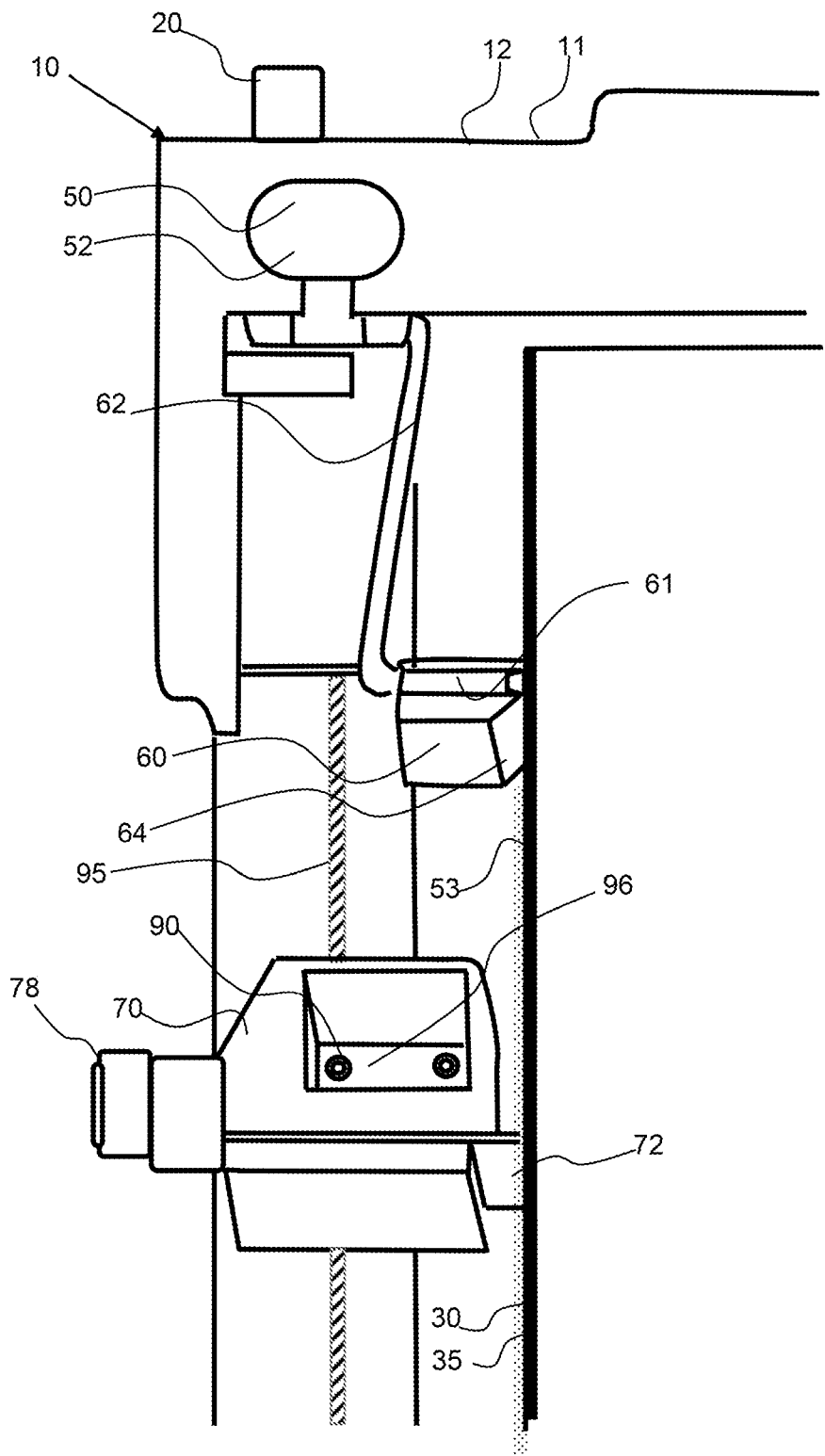
FIG. 6 shows an enlarged cross-sectional view of the fluid applicator and wiper assembly of an exemplary kiosk screen disinfecting system.
Figure 7:
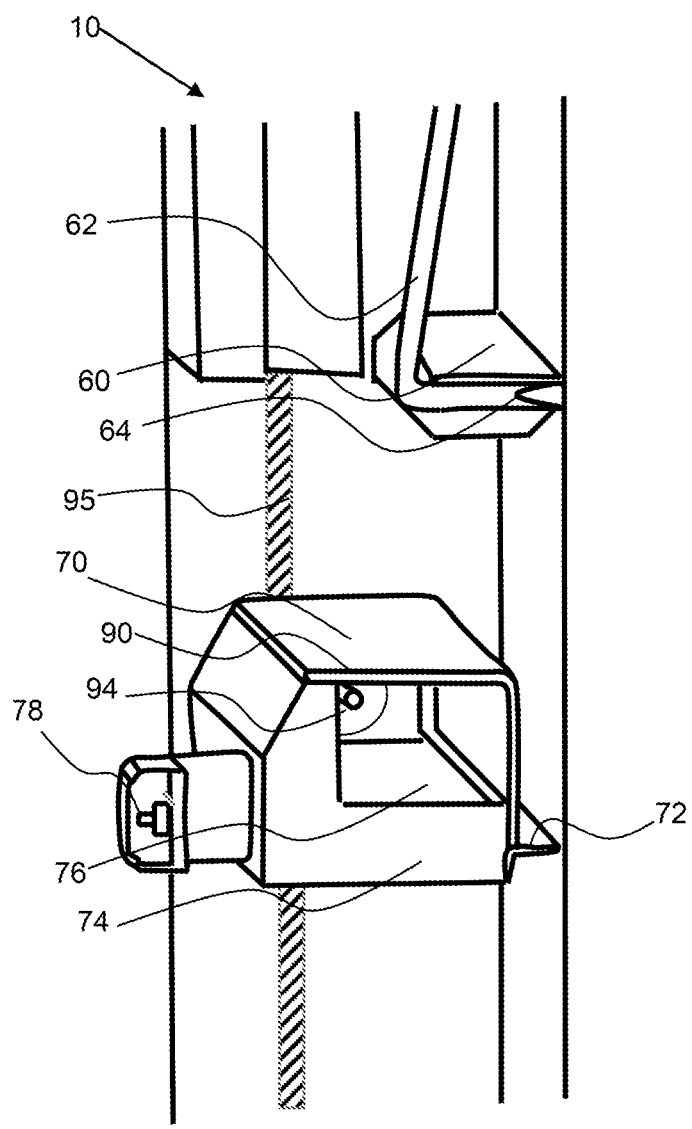
FIG. 7 shows an enlarged cross-sectional view of the fluid applicator and wiper assembly of an exemplary kiosk screen disinfecting system.

Referring now to FIGS. 5 to 7, and exemplary fluid applicator 60 comprise a fluid applicator house 61 and one or more spray heads 64 to dispense disinfecting fluid onto the kiosk screen 30, or touch screen. The wiper assembly 70 is configured to spread or wipe this applied disinfecting fluid 53 over the screen via the wiper 72. The wiper actuator 90 moves the wiper assembly 70 through a rack and pinion assembly 92 comprising a gear 94 and a rack 95. A motor 96 may drive the gear to move the wiper assembly up and down. The disinfecting fluid 52 may be retained in a disinfecting fluid reservoir 50 and may flow to the fluid applicator 60 through a fluid conduit 62.

Figure 8:
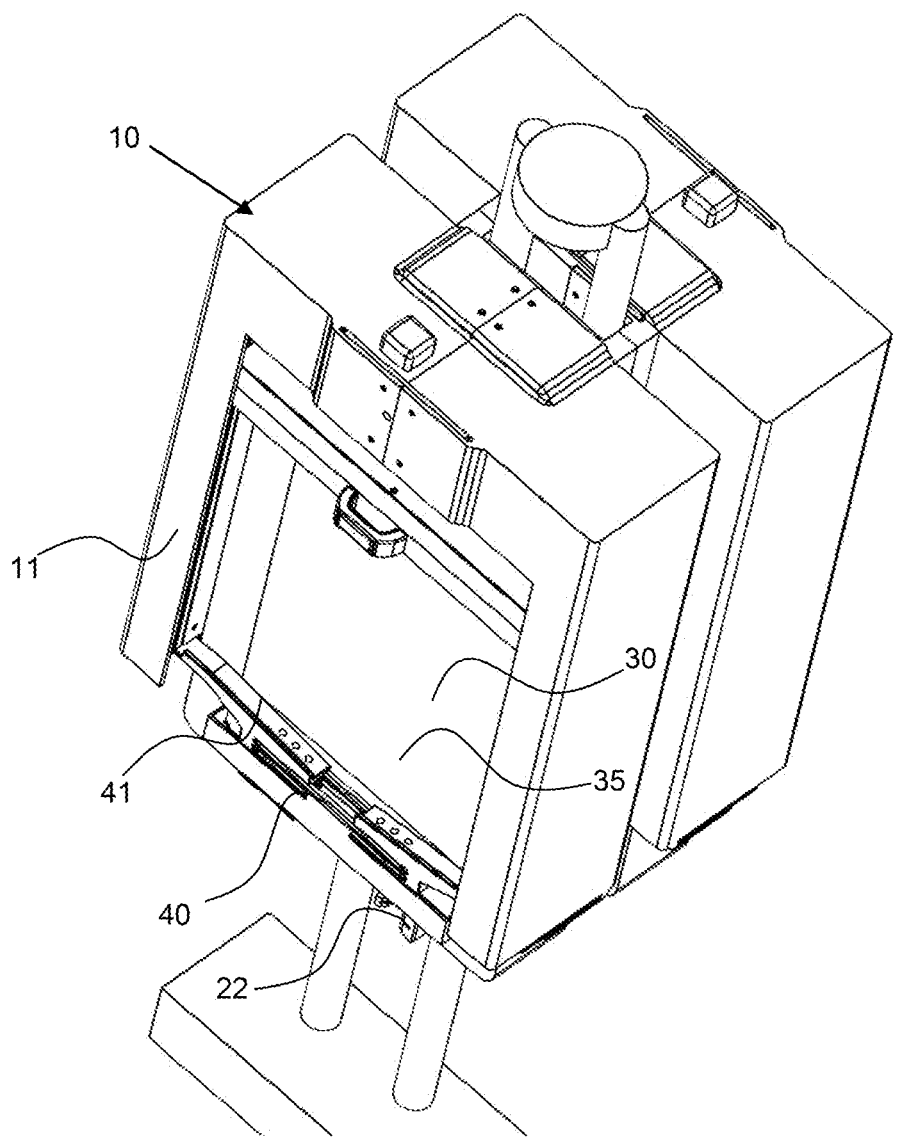
FIG. 8 shows a cross sectional view an exemplary kiosk screen disinfecting system and the collection reservoirs for collecting disinfecting fluid that has been wiped down over the kiosk screen.

As shown in FIG. 8, an exemplary kiosk screen disinfecting system 10 has a collection reservoir 40 for collecting disinfecting fluid that has been wiped down over the kiosk screen. Collection diverters 41 may have apertures to allow the disinfecting fluid to flow through the diverted and into the collection reservoir. A collected fluid pump, may be configured to pump collected fluid back to the disinfecting fluid reservoir.

Figure 9:
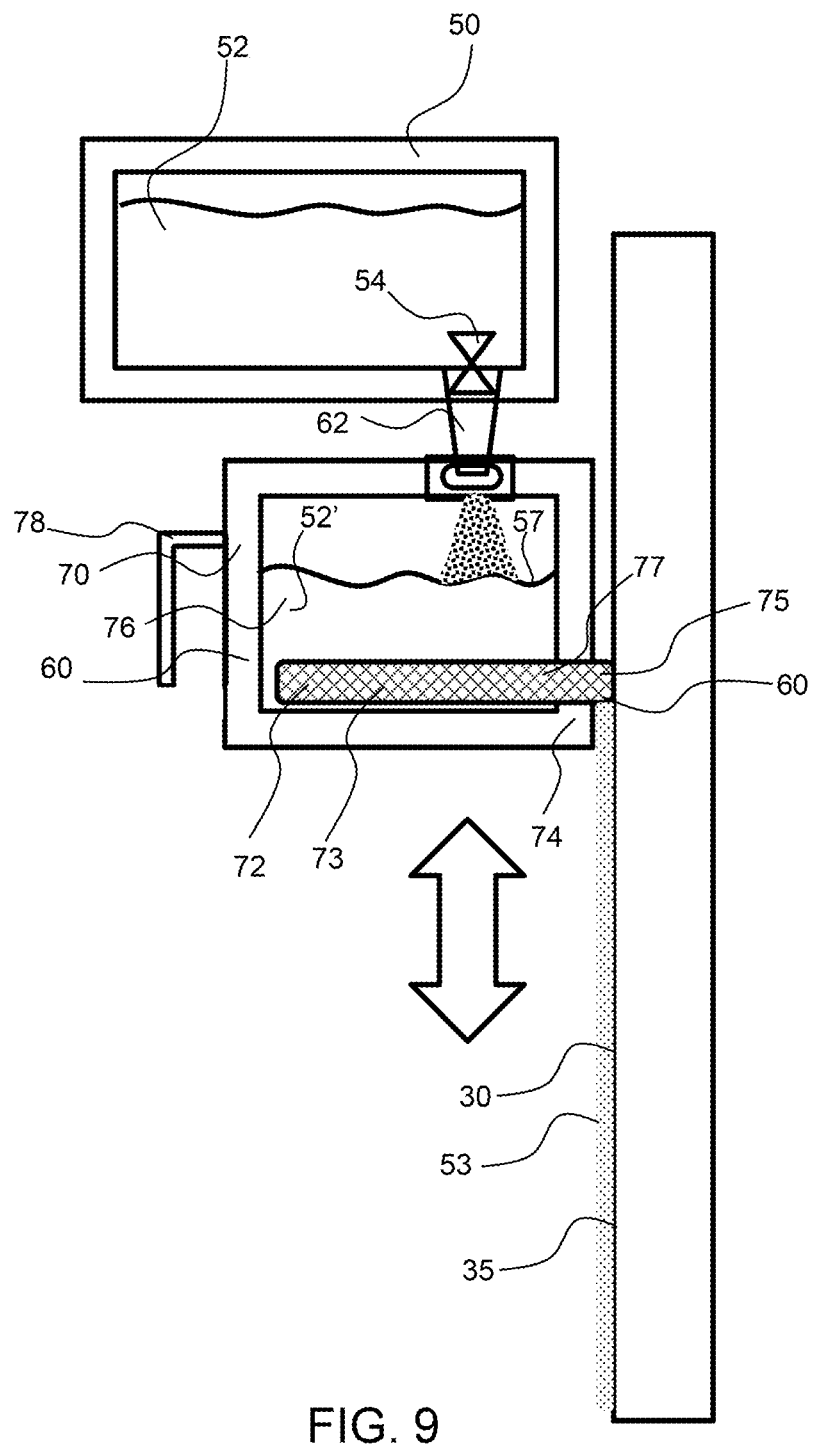
FIG. 9 shows a cross sectional view an exemplary kiosk screen disinfecting system having a wick-wiper in fluid communication with a disinfecting fluid reservoir to keep the wick-wiper moist with disinfecting fluid.
Figure 10:
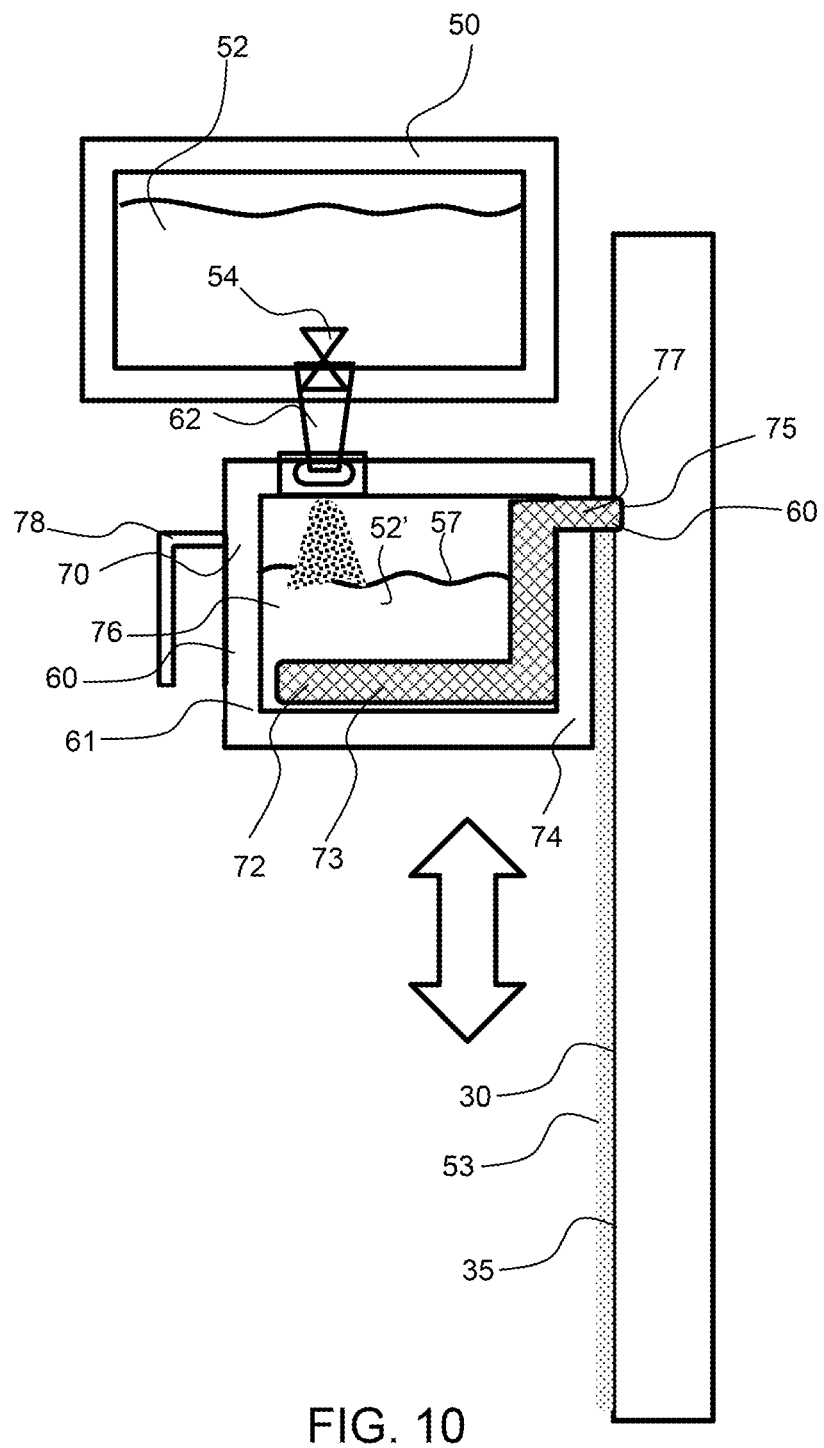
FIG. 10 shows a cross sectional view an exemplary kiosk screen disinfecting system having a wick-wiper that extends out of an applicator opening configured up above a disinfecting fluid reservoir to prevent leakage of disinfecting fluid.
Figure 11:
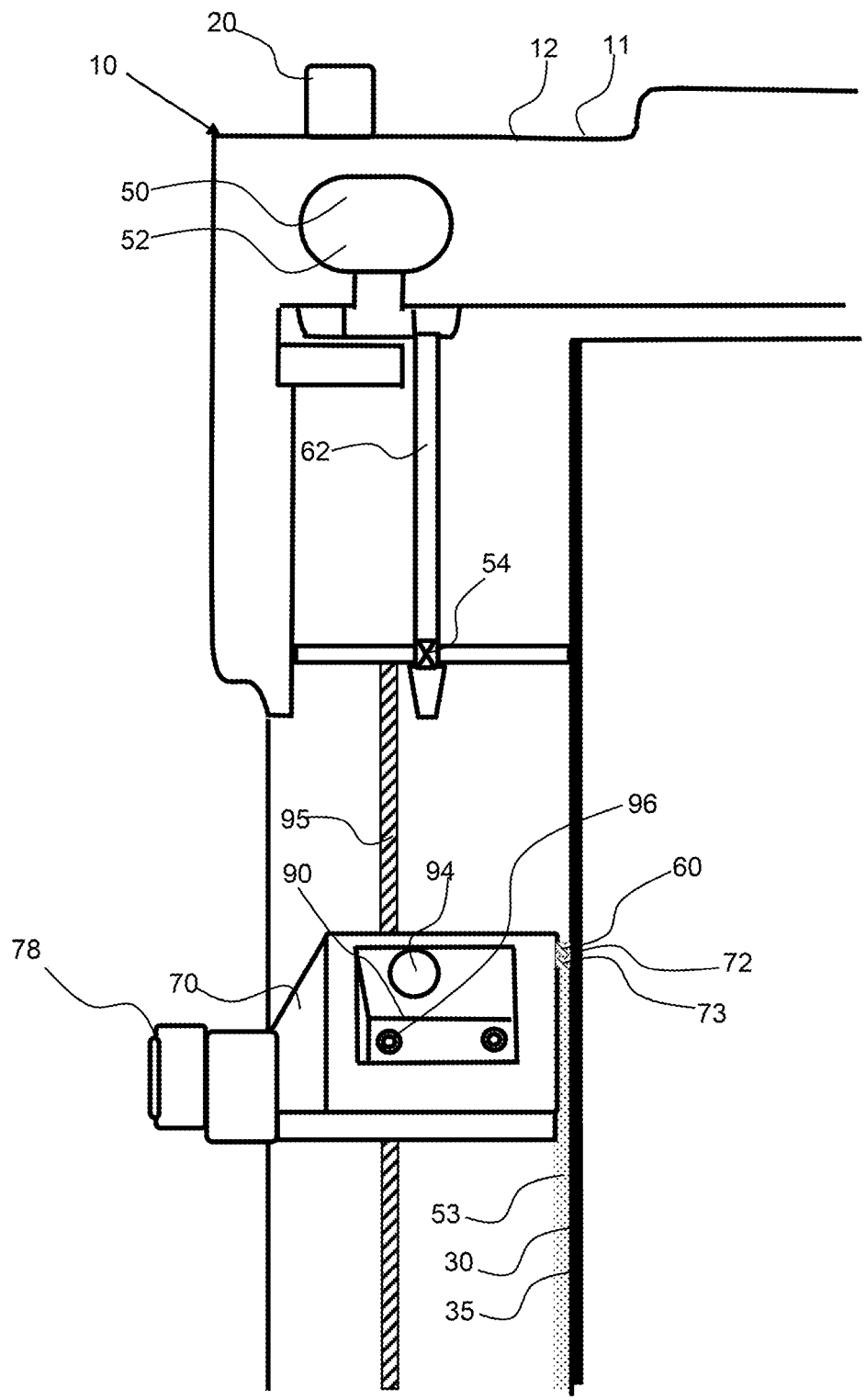
FIG. 11 shows a cross-sectional view of the fluid applicator that incorporates a wiper assembly of an exemplary kiosk screen disinfecting system.

Referring now to FIGS. 9 to 11, an exemplary kiosk screen disinfecting system 10 is configured with a fluid applicator 60, wiper 72 that is a wick-wiper 73 that absorbs and wicks disinfecting fluid 52' from the wiper reservoir 76. The wick-wiper 73 is in fluid communication with disinfection fluid 52' within the wiper reservoir 76. As shown in FIG. 10, the applicator opening 77 is configured above the disinfecting fluid level 57, in the wiper retainer 74, whereby the disinfecting fluid 52' is wicked up from the wiper reservoir 76 by with wick-wiper 73 on is dispensed onto the kiosk screen 30. This location of the applicator opening 77 above the fluid level 57 prevents leakage of disinfecting fluid from the wiper reservoir. The disinfecting fluid wicks through the wick-wiper to keep the exposed wick-wiper 75 portion moist. The applied disinfecting fluid 53 disinfects the kiosk screen, which is a touch screen 35. This wick-wiper comprises a wicking material, such as a sponge, foam or fabric, to wick the disinfecting fluid to the wick-wiper 73, to keep it moist for application to the kiosk screen 30. The wick wiper extends out of the wiper reservoir 76 to create an exposed wick-wiper portion 75. This small area of exposed wick-wiper may reduce the amount of disinfecting fluid that evaporates. As the disinfecting fluid level in the wiper assembly 70 and wiper reservoir 76 is reduced, additional disinfecting fluid 52 may be added from the disinfecting fluid reservoir 50 through a fluid conduit 62 which may have a reservoir valve 54 that opens to allow the disinfecting fluid 52 to flow into the wiper reservoir 76. A fluid conduit 62 may extend between the disinfecting fluid reservoir 50 into the wiper reservoir 76. The reservoir valve 54 may be opened when the wiper assembly 70 is moved up into a refill position, that engages and opens the reservoir valve 54. This refill position may occur between disinfecting cycles of the wiper assembly up and down along the kiosk screen 30. The fluid conduit may detach from the wiper reservoir when the wipe reservoir moved over the kiosk screen to disinfect the kiosk screen. The reservoir valve may open when the disinfecting fluid level in the wiper assembly or wiper retainer drops below a threshold level.

As shown in FIG. 11, the wiper actuator 90 moves the wiper assembly 70 through a rack and pinion assembly 92 comprising a gear 94 and a rack 95. A motor 96 may drive the gear to move the wiper assembly up and down. The disinfecting fluid 52 may be retained in a disinfecting fluid reservoir 50 and may flow to the fluid applicator 60 through a fluid conduit 62. The reservoir valve may be opened by the wiper assembly, when it moves up after a disinfecting cycle.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of disinfecting a kiosk screen comprising:
   a) providing a kiosk screen disinfecting system comprising:
      i) disinfecting fluid;
      ii) a kiosk screen having a height of at least 40 cm and a width of at least 30 cm;
      iii) a disinfecting fluid reservoir for retaining said disinfecting fluid;
      iv) a wiper assembly comprising:
         a wiper reservoir for retaining a portion of said disinfecting fluid;
         an applicator opening in said wiper reservoir;
         a wiper in contact with the disinfecting fluid in said wiper reservoir and extending out through said applicator opening;
         wherein said wiper is configured to contact the kiosk screen and spreads the disinfecting fluid over the kiosk screen; and
      v) a wiper actuator configured to move the wiper assembly over the kiosk screen;
   b) applying the disinfectant fluid to the kiosk screen; and
   c) actuating the wiper assembly with the wiper actuator to spread the disinfecting fluid over the kiosk screen;
   wherein the kiosk screen is a touch screen for ordering items for purchase; and
   wherein the kiosk screen is disinfected by said contact with the disinfecting fluid.

2. The method of disinfecting a kiosk screen of claim 1, wherein the applicator opening is configured above the disinfecting fluid in the wiper reservoir.

3. The method of disinfecting a kiosk screen of claim 1, wherein the wiper is a wick-wiper that wicks the disinfecting fluid from the wiper reservoir into the wick-wiper, wherein the wick-wiper absorbs the disinfecting fluid from the wiper reservoir and dispenses the absorbed disinfecting fluid onto the kiosk screen.

4. The method of disinfecting a kiosk screen of claim 3, wherein the wick-wiper comprises a fabric.

5. The method of disinfecting a kiosk screen of claim 1, further comprising a fluid conduit that extends between the disinfecting fluid reservoir and the wiper reservoir and wherein disinfecting fluid from the disinfecting fluid reservoir is transferred into the wiper reservoir.

6. The method of disinfecting a kiosk screen of claim 5, further comprising a reservoir valve to the fluid conduit that automatically opens to allow disinfecting fluid to flow through said fluid conduit when the wiper reservoir has a disinfecting fluid level that is below a threshold limit.

7. The method of disinfecting a kiosk screen of claim 6, wherein the fluid conduit detaches from the wiper reservoir when the wiper reservoir is moved over the kiosk screen to apply disinfecting fluid to said kiosk screen.

8. The method of disinfecting a kiosk screen of claim 1, wherein the applicator opening has a height of no more than 2.5 cm.

9. The method of disinfecting a kiosk screen of claim 1, further comprising a user sensor to detect the presence of a user proximal to the kiosk screen.

10. The method of disinfecting a kiosk screen of claim 9, wherein the wiper assembly moves over the kiosk screen when said user is detected proximal to the kiosk screen.

11. The method of disinfecting a kiosk screen of claim 1, wherein the disinfecting kiosk screen system further comprises a computer to enter an order by a user.

12. The method of disinfecting a kiosk screen of claim 11, wherein the wiper assembly moves over the kiosk screen when said order is entered.

13. The method of disinfecting a kiosk screen of claim 12, wherein the disinfecting kiosk screen system further comprises a wiper actuator comprising a gear and a motor that moves the gear to move the wiper assembly up and down along the kiosk touch screen.

14. The method of disinfecting a kiosk screen of claim 11, wherein the touchscreen displays a disinfecting message after said order is entered and wherein the disinfecting kiosk screen system requires the wiper assembly to be manually moved over the kiosk screen before a ticket for said order is provided.

15. The method of disinfecting a kiosk screen of claim 1, wherein the disinfectant fluid comprises a volatile organic compound.

16. The method of disinfecting a kiosk screen of claim 15, wherein the disinfectant fluid comprises isopropanol.

17. The method of disinfecting a kiosk screen of claim 15, wherein the disinfectant fluid comprises ethanol.

* * * * *